United States Patent [19]

Rabiller-Baudry et al.

[11] Patent Number: 5,157,174

[45] Date of Patent: Oct. 20, 1992

[54] TERNARY MOLYBDENUM CHALCOGENIDE OXYCHLORINATION CATALYSTS

[75] Inventors: Murielle Rabiller-Baudry, Rennes; Annick Faure, Venissieux; Jean Lesparre, Champ sur Drac; Marcel Sergent, Cesson-Sevigne; Roger Chevrel, Hede, all of France

[73] Assignee: Atochem, Puteaux, France

[21] Appl. No.: 769,813

[22] Filed: Oct. 2, 1991

[30] Foreign Application Priority Data

Oct. 2, 1990 [FR] France ................... 90 12116

[51] Int. Cl.$^5$ ................... C07C 17/154; C07C 17/151
[52] U.S. Cl. ................... 570/245; 570/243; 570/186; 570/203; 570/224; 570/101
[58] Field of Search ............... 570/243, 245, 186, 203, 570/224, 101

[56] References Cited

U.S. PATENT DOCUMENTS 3,796,795 3/1974 Urban et al. .
4,560,470 12/1985 McCarty et al. .

FOREIGN PATENT DOCUMENTS 0335987 10/1989 European Pat. Off. .

Primary Examiner—Howard T. Mars
Attorney, Agent, or Firm—Burns, Doane, Swecker & Mathis

[57] ABSTRACT

Hydrocarbons are oxychlorinated by reaction with gaseous HCl and an oxygen-containing gas, in the presence of a catalytically effective amount of a ternary copper/molybdenum chalcogenide having the formula:

$$Cu_xMo_6Ch_8$$

wherein x is a number ranging up to 4 and Ch is sulfur, selenium or tellurium, advantageously, in the added presence of a known oxychlorination catalyst and, optionally, a proportion of inert particulate solids; the ternary molybdenum chalcogenides of the formula $M_xMo_6S_8$ are also prepared, wherein M is a metal, advantageously by the hydrogen gas reduction of intimate admixture of $MoS_2$ and metal M, or precursors thereof.

10 Claims, No Drawings

TERNARY MOLYBDENUM CHALCOGENIDE OXYCHLORINATION CATALYSTS

BACKGROUND OF THE INVENTION

1. Field of the Invention

The present invention relates to the oxychlorination of hydrocarbons in the presence of catalysts based on ternary molybdenum chalcogenides.

2. Description of the Prior Art 1,2-Dichloroethane (D12) is a compound that is produced industrially at a rate of several million ions per year; it is converted by pyrolysis into vinyl chloride monomer (VCM) and hydrochloric acid (HCl). VCM is polymerized into poly(vinyl chloride) (or PVC) which is widely in demand. The HCl produced by the pyrolysis is separated from the VCM and is then contacted with ethylene and oxygen in the presence of a catalyst to yield D12; this is the oxychlorination reaction. This reaction is very general and may be carried out using a wide variety of the hydrocarbons. Oxychlorination has been described in numerous patents, in particular in FR-2,063,365, FR-2,260,55, FR-2,242,143, FR-2,213,259 and FR-2,125,748. The catalyst typically is a copper salt deposited onto alumina powder.

SUMMARY OF THE INVENTION

A major object of the present invention is the provision of an improved process for the oxychlorination of hydrocarbons in the presence of certain catalysts comprising ternary molybdenum chalcogenides containing copper.

Briefly, the present invention features the oxychlorination of a hydrocarbon to produce a chlorinated hydrocarbon, comprising passing the hydrocarbon, a gas containing oxygen and gaseous hydrochloric acid over a charge which comprises a catalytically effective amount of a ternary molybdenum chalcogenide containing copper, having the formula:

$$Cu_xMo_6Ch_8$$

wherein x is a number ranging up to 4 and Ch represents sulfur, selenium or tellurium.

DETAILED DESCRIPTION OF THE PREFERRED EMBODIMENTS OF THE INVENTION

More particularly according to the present invention, the chalcogenides may be pseudo-molecular compounds based on the $Mo_6Ch_8$ structural unit, which constitutes a host lattice having a rigid structure, while developing intersecting channels in the three dimensions in which the Cu cations are situated.

These pseudo-molecular phases may also be represented as several entangled lattices; a lattice of metallic atoms (the $Mo_6$ octahedron) inscribed within an anionic pseudo-cubic chalcogen lattice (the $Ch_8$ "cube") and, finally, a network of channels which develops between the $Mo_6Ch_8$ structural units. These channels are occupied by the Cu cations, which stabilize the structure. The chalcogenides crystallize in the hexagonal-rhombohedral system.

They are typically in powder or granular form.

The hydrocarbon to be oxychlorinated may be a mixture of several hydrocarbons selected from among the $C_1$-$C_{20}$ aliphatic hydrocarbons, the cycloaliphatic hydrocarbons having up to 12 carbon atoms and the aromatic hydrocarbons having up to four condensed benzene nuclei, as well as the chlorine substituted derivatives thereof. Exemplary thereof are methane, ethane, propane, ethylene and propylene. Ethylene is particularly representative.

The oxygen-containing gas is advantageously air, but air depleted or enriched in oxygen may also be used.

The focus of oxychlorination is essentially to use hydrochloric acid as the source of chlorine. The amount of oxygen and hydrocarbon is thus adjusted to essentially stoichiometrically produce the chlorinated hydrocarbon by consuming the maximum of HCl and hydrocarbon.

In the case of ethylene, the reaction is:

$$C_2H_4 + \tfrac{1}{2}O_2 + 2\,HCl \rightarrow C_2H_4Cl_2\,(D12) + H_2O$$

It may be carried out in a fixed bed or fluidized bed, but a fluidized bed is preferred.

If the reaction is carried out using a catalyst in a fluidized bed, the temperature at which oxychlorination proceeds typically ranges from 150° to 450° C. Preferably, the temperature ranges from 200° to 300° C.

The pressure at which the reaction is carried out is not critical in and of itself. Typically such pressures range from 1 to 10 atm and preferably from 1 to 8 atm.

The velocity of the fluidization of the catalytic compositions is also not critical in and of itself and depends essentially on the grain size distribution of the catalyst and the dimensions of the apparatus. Generally, velocities ranging from 5 to 100 cm/s and preferably from 10 to 50 cm/s are employed.

Finally, the proportions of the reagents used are generally the same as those used in the known processes. Typically, a slight excess of ethylene relative to the amount of HCl is employed. However, the catalytic compositions of the invention permit conducting the reaction at near stoichiometry, or even using an excess of HCl.

All of these general operating conditions are known to the prior art.

One advantage of the present invention is that the catalyst is much more mechanically resistant than the oxychlorination catalysts of the prior art, albeit the performance of which relative to the conversion of the hydrocarbon and the hydrochloric acid and the dichloroethane selectivity is not outstanding.

However, it has now been determined that if known oxychlorination catalysts are added to the subject chalcogenides, performances superior to those of the known catalysts are obtained. The known catalysts, designated "conventional catalysts", consist of copper deposited onto a porous support, which may be alumina, i.e., the operation is carried out using a mixture of he chalcogenides and conventional catalysts, for example, those described in FR-2,125,748, FR-2,063,365, FR-2,141,452, EP-57,796, EP-62,320, EP-119,933 and EP-255,156.

The known catalysts are advantageously powders essentially based on alumina having a grain size distribution ranging from 20 to 200 μm and a specific surface area ranging from 90 to 450 m²/g and preferably from 30 to 90 μm and 250 to 400 m²/g. These powders are impregnated with copper or a copper salt in an amount of up to 10%, preferably from 3% to 10% by weight of copper relative to the final product catalyst.

It has also been determined that the subject chalcogenides may be used in combination with oxychlorination catalysts which themselves comprise a mixture of an oxychlorination catalyst and a catalytically and chemically inert solid material, i.e., the operation is carried out using a mixture of a chalcogenide, a conventional oxychlorination catalyst and an inert material. Oxychlorination catalysts comprising a mixture of an active catalyst and an inert material are descried in FR-2,242,143.

Exemplary catalytically and chemically inert materials include glass or silica microbeads, alpha alumina and preferably silica sand, the latter being in the natural state and the size distribution of the particles of which being suitable for fixed or fluidized bed applications.

Advantageously, the particle size of the inert material ranges from 20 to 200 μm.

The amount of the inert material may vary over wide limits. Advantageously, the amount of inerts ranges from 1 to 20 times by weight the amount of the catalyst, i.e., the entirety of the chalcogenide and the conventional oxychlorination catalyst.

It too has been determined that the subject chalcogenides may be used in combination with nonimpregnated catalyst supports, i.e., alumina powders containing no copper. These include, for example, powders having a grain size distribution ranging from 20 to 200 μm and a specific surface area ranging from 90 to 450 m²/g, such as those described above, but not being impregnated with copper.

It is also possible to combine the nonimpregnated catalyst support with a catalytically and chemically inert material as described above, e.g., glass or silica microbeads, silica, alpha alumina, etc.

The oxychlorination process according to the invention may thus be carried out using the following catalytic charges:

(i) the subject chalcogenides,
(ii) a mixture of such chalcogenides and conventional oxychlorination catalysts and, optionally, a catalytically and chemically inert material,
(iii) a mixture of such chalcogenides and a nonimpregnated catalyst support and, optionally, a catalytically and chemically inert material.

These catalytic charges may be present in fixed or fluidized beds. The aforementioned chalcogenides, i.e., the $Cu_xMo_6Ch_8$ chalcogenides, are per se known, J. Solid State Chem., 3, 515-519 (1971), while the catalytic charges comprising a mixture of such chalcogenides and conventional oxychlorination catalysts and, optionally, a catalytically and chemically inert material, are novel compositions.

Likewise novel are the mixtures of such chalcogenides and a nonimpregnated catalyst support and, optionally, a catalytically and chemically inert material.

The present invention also features such catalytic charges, per se.

The chalcogenides may be prepared by a process descried in J. Solid State Chem., 3, 515-519 (1971).

The different constituents in the form of elements, compounds or sulfides are intimately admixed in an agate mortar, the powder then pelletized, introduced into a silica tube, and sealed under a dynamic Vacuum (10⁻² mmHg, argon). The chalcogenide is produced after heating at approximately 750° C. In order to obtain a pure product, it is frequently useful to carry out several cycles: grinding—pelleting—heat treatment. All of these operations are performed in a controlled atmosphere, in an enclosure under argon.

Using this process, only small quantities can be prepared. However, the present invention also features a process that may be carried out on an industrial scale and which permits production of an entire family of chalcogenides.

Thus, this invention also features a process for the preparation of chalcogenides of the formula $M_xMo_6S_8$ wherein x is a number ranging up to 4 and M is a metal, comprising reducing, with hydrogen, a mixture of $MoS_2$ and of the metal M, or of the precursors thereof. The metal M may, for example, be an alkali or alkaline earth metal, a metal of Group 3b of the Periodic Table, a lanthanide, an actinide, lead, tin, magnesium, zinc, manganese, cadmium, copper, nickel, iron or cobalt.

It is also within the scope of the invention to use $MoS_2$ and a precursor of metal M, a mixture of the metal M and a precursor of $MoS_2$, and a mixture of $MoS_2$, a precursor of $MoS_2$ and a metal M, or any combination thereof. The reduction with hydrogen may be carried out simply by contacting the $MoS_2$/M mixture with hydrogen.

Any hydrogen pressure may be employed and the reaction temperature advantageously ranges from 450° to 1,100° C. The precursors of $MoS_2$ and M are compounds which, under the hydrogenation conditions, yield $MoS_2$ and M. The precursor of $MoS_2$ may, for example, be:

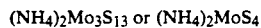

$(NH_4)_2Mo_3S_{13}$ or $(NH_4)_2MoS_4$

The precursor of the metal M may be a salt, such as a chloride, a sulfide, a nitrate, a sulfate or an acetate. The proportions of $MoS_2$ and M in the mixture prior to hydrogenation are adjusted as a function of the chalcogenide desired and the specific reactivities of M or precursor thereof. Mixed precursors may also be used, for example $Cu(NH_4)MoS_4$. Depending on the chalcogenides to be produced, they may be used either alone or with other precursors of the metal or of $MoS_2$.

It is not necessary to separate the $MoS_2$ or the M prior to the preparation of the chalcogenide, i.e., the reagents $MoS_2$ and M may be produced in situ and the reaction then continued until the chalcogenide is obtained.

The chalcogenides $M_xMo_6S_8$ have the same structure as the aforementioned chalcogenides $Cu_xMo_6CH_8$, i.e., the $Mo_6S_8$ structural unit is again present; it creates a host lattice having a rigid structure. These chalcogenides crystallize in the hexagonal rhombohedral system.

The invention also features a process for the preparation of chalcogenides of the formula $M_xMo_6S_8$ wherein x is a number ranging up to 4 and M is a metal, comprising inserting a metal M into an existing $Mo_6S_8$ matrix in the presence of a gaseous flowstream.

The metal may be used as such, or in the form of a salt thereof. It suffices to mix the metal and the $Mo_6S_8$, each preferably being in a divided state, and to heat the reaction mixture while sweeping the gaseous flowstream therethrough. It is advantageous to use nitrogen for such purpose. The temperature of the operation advantageously ranges from 150° to 400° C.

The present invention also features a chalcogenide of the formula $M_xMo_6S_8$, wherein x is a number ranging up to 4 and M is a metal, deposited onto a porous support substrate.

A process for the preparation of such chalcogenides has been described above. The porous support substrate may be alumina, silica, silicoalumina, graphite, carbon, $TiO_2$, $ZrO_2$ and, in general, any material useful as a catalyst support. Advantageously, alumina powders having a grain size distribution ranging from 20 to 200 μm and a specific surface area ranging from 90 to 450 $m^2/g$ and preferably from 30 to 90 μm and from 250 to 400 $m^2/g$, are used.

Supported chalcogenides with copper as the metal M are useful as catalysts of the oxychlorination of hydrocarbons.

The supported chalcogenides may be prepared by impregnating the support substrate with precursors of $MoS_2$ and of the metal M and then reducing the impregnated substrate with hydrogen. The precursors of $MoS_2$ and M are those described above. It is also possible to prepare the precursor in situ in the pores of the support, for example $(NH_4)_2MoS_4$ may be prepared by reacting the paramolybdate $(NH_4)_2Mo_7O_{24}.4H_2O$ in solution in $NH_4OH$ with $H_2S$. For example, $(NH_4)_2Mo_3S_{13}$ may be prepared by reacting $(NH_4)_6Mo_7O_{24}.4H_2O$ with an ammonium polysulfide. The latter is prepared by reacting $H_2S$ with a solution of $NH_4OH$ and sulfur (*Chem. Ber.*, 112, 778-780 (9179)).

Supported chalcogenides may also be prepared from a material already deposited onto a porous support substrate, but not in the form of a chalcogenide.

It is possible to thus use, for example, an existing hydrodesulfurization catalyst, such as the alloy Ni-Mo-S or Co-Mo-S deposited onto alumina. It suffices to then conduct the hydrogen reduction of such material.

In order to further illustrate the present invention and the advantages thereof, the following specific examples are given, it being understood that same are intended only as illustrative and in nowise limitative.

EXAMPLE 1

Synthesis of $Cu_{2.5}Mo_6S_8$ in a Sealed Tube

The following powders were intimately admixed:

$2.5\ Cu + 4\ MoS_2 + 2\ Mo$

The powders were pelletized and introduced into a sealed silica tube under a dynamic vacuum $10^{-2}$ mmHg pressure). The mixture was heated at 800° C. for 70 hours. The powder obtained had an RX diffraction pattern. The product crystallized in the hexagonal rhombohedral system.

The lattice parameters of the hexagonal system: a=9.6 Å, c=10.2 Å ($MoS_2$ may remain as an impurity).

EXAMPLE 2

Synthesis of $Cu_2Mo_6S_8$ by Hydrogen Reduction 0.4107 g $(NH_4)_2MoS_4$ + 0.0901 g $CuCl_2 2H_2O$ Powders of the above were intimately admixed and ground in an agate mortar, and then placed into a silica boat. Reduction thereof was carried out in a horizontal furnace at 700° C. for 89 hours, with a $H_2$ flow rate of 1.5 ml/s; identification by RX; hexagonal lattice parameters: a=9.60 Å, c=10.22 Å (if any $MoS_2$ remains, the reaction is not complete and should be continued).

The $MoS_2$ was identified by the RX diffraction pattern:
ASTM No. 6-0097
and
No. 9-312

EXAMPLE 3

Synthesis of $Cu_xMo_6S_8/Al_2O_3$

Chalcogenide deposited on a porous support (1) Impregnation of precursors:

0.4107 g $(NH_4)_2.MoS_4$ was dissolved in 6.5 ml concentrated aqueous ammonia and 12 g $Al_2O_3$ were added. The solution was maintained for 24 hours in a desiccator filled with $P_2O_5$ and under vacuum. It was then reduced in a horizontal furnace, under $H_2$ for 8 min, with the temperature increasing from ambient to 400° C. and at a $H_2$ flow rate of 0.5 ml/s=product A.

0.0901 g $CuCl_2.2H_2O$ was dissolved in 8 ml $NH_4OH$ and product A was added thereto. The solution was maintained for 75 hours in a dessicator filled with $P_2O_5$, under vacuum. The entire mass was reduced under $H_2$, 1.5 ml/s, for 89 hours, in a horizontal furnace. A fraction of granules was removed. It was placed in a sealed silica tube under a dynamic vacuum and heat treated for 24 hours at 900° C.

(2) Two different heptamolybdate processes:

(a) Air Method:

1.5 g $(NH_4)_6Mo_7O_{24}.4H_2O$ and 1.36 g $Cu(NO_3)_2.3H_2O$ were dissolved in 5 ml concentrated aqueous ammonia. 10 g $Al_2O_3$ were added and the solution was maintained in the ambient air for 1 hour, 30 minutes. It was heated in air in an oven at 120° C. for 2 hours. Calcination in air was then carried out at 350° C. for 2 hours. A fraction of $\approx$10 granules (weight<1 g) was then calcined in air at 500° C. for 2 hours. It was then sulfurized with $H_2S$ at 400° C. for 30 min and reduced with $H_2$ at 1.5 ml/s, for 49 hours. Identification by EXAFS: K threshold of Mo of a mixture of $Cu_xMo_6S_8$ and $MoS_2$ (the value of x was not known, but x$\geq$2.

(b) $H_2$, $N_2$ Method:

1.5 g $(NH_4)_6Mo_7O_{24}.4H_2O$ and 1.36 g $Cu(NO_3)_2.3H_2O$ were dissolved in 5 ml $NH_4OH$. 10 g $Al_2O_3$ were added and the solution was maintained in ambient air for 1 hour, 30 min. It was swept with nitrogen at 120° C. for 3 hours, then with hydrogen for 16 hours at 200° C., for 2 hours at 240° C., and for 67 hours at 245° C. This was followed by a nitrogen sweep at 500° C. for 24 hours.

A fraction of $\approx$10 granules ($\approx$500 mg) was sulfurized with $H_2S$ at 400° C. for 30 min. It was then reduced under $H_2$, at a flow rate of 1.5 ml/s, for 49 and 89 hours. Identification by EXAFS: K threshold of the Mo of a mixture of $Cu_xMo_6S_8$ and $MoS_2$.

EXAFS measurements at the K threshold of Mo result from the comparison of the impregnated products described above and crystallized powders of reference $Cu_4Mo_6S_8$ and $MoS_2$ (syntheses in sealed tube).

Measurements were conducted on the reference compounds, as no literature data exist for $Cu_4Mo_6S_8$ in EXAFS at the K threshold of Mo. Data exist for $MoS_2$.

EXAMPLE 4

Oxychlorination experiments were carried out in the following apparatus. The reactor was a vertical glass tube charged with the catalyst. Gas was introduced at the base to fluidize the catalyst. Thermocouples placed in a glass enclosure in the center of the reactor permitted monitoring of the evolution of the temperature both in time and according to the height of the catalyst bed. At the outlet of the reactor, the gases were transferred through a recovery column, in which all of the unreacted HCl was recovered by washing with distilled water. The HCl was contained in a decanter tube. The remainder of the gas then passed successively through a water cooler, a brine cooler (t= −5° C.) wherein the solvents recovered condensed in another decanter tube, and were then swept through sampling tubes for the determination of the remaining gases prior to inlet into a volume counter, the measurement of which yielded the gaseous flow at the outlet. The determination of the temperature at this level was used to evaluate the correction necessary to attain NTP (normal temperature and pressure) conditions. The atmospheric pressure was determined from a mercury manometer.

Three types of different sampling and analyses were carried out:

(i) an aqueous solution of HCl, (ii) condensed solvents, among them D12, (iii) exit gases: CO, $CO_2$, D12 and unreacted reagents, i.e., $C_2H_4$ and air.

The following were compared: (a) a conventional catalyst consisting of alumina having a specific surface area of 357 $m^2/g$, a mean diameter of 53 $\mu m$, a pore volume of 33 $cm^3/100$ g, impregnated with copper chloride, and which included an inert material, i.e., silica having a mean diameter of 50 $\mu m$ and ranging from 20 to 300 $\mu m$; with (b) a catalyst constituted by a chalcogenide $Cu_{2.5}Mo_6S_8$, alumina and an inert material (silica). The alumina and the silica had the same characteristics as given above, except for the absence of copper.

The results obtained are reported in Table 1.

TABLE 1

| Operating Conditions: | | | |
|---|---|---|---|
| Feed: | $C_2H_4$ | 4.4 | Nl/h |
|  | Air | 16.2 | Nl/h |
|  | HCl | 8.6 | Nl/h |
| Reactor diameter: |  | 20 | mm |

|  | $Cu_{2.5}Mo_6S_8$ | 4.25 g | Alumina with Cu | 9.70 g |
|---|---|---|---|---|
|  | $Al_2O_3$ | 6.00 g | $SiO_2$ | 23.60 g |
|  | $SiO_2$ | 22.60 g | conventional catalyst |  |
| Cu quantity (g) | 0.68 |  | 0.58 |  |
| T (°C.) | 230 |  | 240 |  |
| Conversion of $C_2H_4$ | 78.5 |  | 72.3 |  |
| Selectivity in D 12 | 99.2 |  | 99.1 |  |

The catalytic charge of this invention provided better conversion and better selectivity (selectivity expressed as the fraction of $C_2H_4$ converted, transformed into D12).

EXAMPLE 5

Oxychlorination

Flow rates at the inlet of the reactor

Air: 12.2 Nl/h; $C_2H_4$:4.4 Nl/h; HCl: 8.6 Nl/h for 1.2 g Cu for 59 g of the catalytic charge in its entirety (Cu included), except for Test 2.

Definitions $X_G$ = proportion of $C_2H_4$ converted
$Y_G$ = proportion of HCl converted
$Z_G$ = proportion of $O_2$ converted List of Tests

| (1) | $Al_2O_3$ | 12.0 g | (2) $Cu_{2.5}Mo_6S_8$ | 63.9 g |
|---|---|---|---|---|
|  | $SiO_2$ | 39.6 g |  |  |
|  | $Cu_{2.5}Mo_6S_8$ | 7.4 g |  |  |
| (4) | $Al_2O_3$ | 51.6 g | (6) same as (4) |  |
|  | $Cu_{2.5}Mo_6S_8$ | 7.4 g |  |  |
| (15) | $Al_2O_3$ | 29.0 g |  |  |
|  | $CuCl_2/Al_2O_3$ (4% Cu) | 30.0 g |  |  |
| (16) | $Al_2O_3$ | 55.8 g |  |  |
|  | $CuCl_2.2H_2O$ | 3.2 g |  |  |

The alumina, whether or not impregnated with copper ($Al_2O_3$), in these tests was identical to that of Example 4, as was the silica.

The results obtained are reported in the following Table 2:

TABLE 2

| Test | Duration | Temp. (°C.) | Retention Time(s) | $X_G$ % | $Y_G$ % | $Z_G$ % | Yield CO + $CO_2$ | Yield C1 + C2 | Selectivity D12 |
|---|---|---|---|---|---|---|---|---|---|
| 1 | 4 h 25 | 249 | 4.5 | 88.3 | 64.9 | 78.6 | 0.7 | 1.7 | 97.3 |
| 2 | 0 h 25 | 264 | 4.8 | 3.1 | 2.1 | 17.1 | 1.7 | 0.3 | 36.0 |
| 4 | 4 h 00 | 216 | 5.9 | 32.2 | 42.8 | 26.1 | 0.8 | 3.1 | 87.9 |
| 6 | 4 h 00 | 249 | 5.6 | 54.4 | 46.5 | 64.2 | 8.5 | 5.0 | 75.2 |
| 16 | 4 h 00 | 241 | 5.8 | 26.6 | 16.9 | 11.3 | 0.4 | 13.5 | 47.8 |

C1 and C2 indicate compounds chlorinated at C1 and C2, other than D12.

EXAMPLE 6

This example relates to the synthesis of $Cu_xMo_6S_8$ by insertion into $Mo_6S_8$ under nitrogen. The synthesis of $Mo_6S_8$ is described in Rev. Chim. Min., 21, 509 (1984).

Cu was introduced into $Mo_6S_8$ under nitrogen at a temperature greater than or equal to 200° C. The starting material Cu could be metallic copper or a copper chloride.

The reagents were in the stoichiometric proportions Mo:Cu=6:x.

EXAMPLE 7

This example relates to the synthesis of $Cu_xMo_6S_8/Al_2O_3$ from an existing catalyst, $MoO_3$, $NiO/Al_2O_3$ (Mo: 9%/Ni+Mo:12%), $Al_2O_3$ having a large specific surface area.

Process 500 mg of charge were sulfurized with $H_2/H_2S$ 15%, at 400° C. for 4 hours.

The material was then reduced under $H_2$ at 800° C. for 66 hours ($H_2$ flow rate equal to or different from 1 ml/s). The product was identified by its diffraction diagram RX after heat treatment in a sealed tube at 900° C. for 24 hours.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a chlorocarbon, comprising oxychlorinating a hydrocarbon with gaseous HCl and an oxygen-containing gas, in the presence of a catalytically effective amount of a ternary copper/molybdenum chalcogenide having the formula:

$$Cu_xMo_6Ch_8$$

wherein x is a number ranging up to 4 and Ch is sulfur, selenium or tellurium.

2. The process as defined by claim 1, wherein said formula, Ch is sulfur.

3. The process as defined by claim 1, carried out in the presence of said ternary copper/molybdenum chalcogenide and an added oxychlorination catalyst.

4. The process as defined by claim 3, carried out in the presence of said ternary copper/molybdenum chalcogenide, said added oxychlorination catalyst and inert particulate solids.

5. The process as defined by claim 3, said added oxychlorination catalyst comprising an alumina support substrate impregnated with copper values.

6. The process as defined by claim 4, said inert particulate solids comprising silica.

7. The process as defined by claim 1, carried out in the presence of said ternary copper/molybdenum chalcogenide and a nonimpregnated catalyst support substrate.

8. The process as defined by claim 7, carried out in the presence of said ternary copper/molybdenum chalcogenide, said nonimpregnated catalyst support substrate and inert particulate solids.

9. The process as defined by claim 1, carried out in a fluidized bed.

10. The process as defined by claim 1, carried out in a fixed bed.

* * * * *